United States Patent
Partika et al.

[11] Patent Number: 5,779,053
[45] Date of Patent: Jul. 14, 1998

[54] SKIN PREPARATION TRAY FOR USE IN SURGICAL PROCEDURES

[75] Inventors: Lawrence Partika, Bridgewater; Vivekanand Arya, Fairview; Christopher Johnson, Ringwood, all of N.J.

[73] Assignee: Becton, Dickinson and Company, Franklin Lakes, N.J.

[21] Appl. No.: 841,878

[22] Filed: May 5, 1997

Related U.S. Application Data

[63] Continuation of Ser. No. 499,340, Jul. 7, 1995, abandoned.

[51] Int. Cl.$^6$ ............................................. B65D 85/62
[52] U.S. Cl. ........................... 206/570; 206/370; 206/564
[58] Field of Search ................................. 206/363, 370, 206/570, 438, 557, 561, 564, 565

[56] References Cited

U.S. PATENT DOCUMENTS

| | | | |
|---|---|---|---|
| 3,987,895 | 10/1976 | Janshidi . | |
| 4,170,300 | 10/1979 | Pick | 206/365 |
| 4,226,328 | 10/1980 | Beddow | 206/364 |
| 4,501,363 | 2/1985 | Isbey, Jr. | 206/570 |
| 4,523,679 | 6/1985 | Paikoff et al. | 206/370 |
| 5,178,282 | 1/1993 | Williams | 206/570 |
| 5,207,325 | 5/1993 | Kennedy | 206/370 |
| 5,424,048 | 6/1995 | Riley | 206/370 |

*Primary Examiner*—Jacob K. Ackun
*Attorney, Agent, or Firm*—Arthur D. Dawson

[57] ABSTRACT

A preparation tray for use in a medical procedure involving a solution and one or more swab implements for applying the solution to a patient. The preparation tray, which may be held in the hand or supported on a surface, may be formed as a removable component of a surgical kit. The preparation tray includes a relatively planar sheet having a pair of opposed sides and various embossments for retaining medical implements such as swabs and solution utilized in the medical procedure. A digit opening may be provided on an opposed side of the sheet to accommodate a user's fingers as the tray is held in the hand. The tray further includes a pressing surface formed between two opposed sides of the sheet that communicates with a basin embossment that holds a quantity of the solution. A user may compress the swab implement against the pressing surface to remove excess solution absorbed by the swab, which is returned to the basin embossment. The pressing surface is supported by the hand of a user so as to avoid flexing of the tray and spillage of the solution during the procedure. The tray is readily manipulable by either left-handed or right-handed users.

17 Claims, 9 Drawing Sheets

SKIN PREPARATION TRAY FOR USE IN SURGICAL PROCEDURES

This is a continuation of application Ser. No. 08/499,340, filed Jul. 7, 1995 and now abandoned.

I. FIELD OF THE INVENTION

The invention relates to an improved skin preparation tray for use in surgical procedures, and more particularly, to an improved skin preparation tray having stability structure and being readily manipulable by both right-handed and left-handed practitioners.

II. BACKGROUND

Prior to commencing surgical intervention on a patient, a practitioner is required to disinfect the skin puncture site to prevent the inadvertent introduction of contaminants through the skin. Disinfection is typically performed with an antimicrobial solution, such as an iodine solution, utilizing a swab implement dipped in the antimicrobial solution. The practitioner normally applies the solution in a circular motion, thereby disinfecting the desired area of the skin. If one swab will not suffice to disinfect the desired area, the practitioner discards a used swab in favor of a fresh one dipped into the solution; once a swab has touched the skin, good practice dictates that it not be re-dipped into the solution.

To assist the practitioner in this endeavor, skin preparation trays are often provided in conjunction with the prepackaged surgical kits utilized by the practitioner during a given surgical procedure. The skin preparation trays, which can be incorporated as a non-removable part of the surgical kit or included as a unit removable from the surgical kit, may feature: a basin area for retaining a quantity of antimicrobial solution, such as iodine solution, normally supplied from an external container source; areas for retaining one or more swab implements; and some type of rigid surface or "pressure pad" area to assist the practitioner in removing excess antimicrobial solution from the swab implement once dipped into the basin. Each of basin area, swab retaining areas, or pressure pad areas may or may not be incorporated together in the integral structure of the skin preparation kit. Examples of surgical kits incorporating integral, non-removable skin preparation trays include U.S. Pat. Nos. 4,170,300, entitled "Dressing Change Kits", and 4,523,679, entitled "Pre-Sterilized Medical Procedure Kit Packages." Examples of surgical kits having removable trays or compartments, some of which retain skin-treating implements, include U.S. Pat. Nos. 4,226,328, entitled "Catheterization Package"; 5,178,282, entitled "Modular Surgical Packaging System"; and 3,987,895, entitled "Disposable Liver Biopsy Tray".

One consideration in designing skin preparation trays is the requirement to isolate the antimicrobial solution from other instruments in the surgical kit, lest the instruments be contaminated with solution inadvertently splashed either from the container source or from the basin itself. For instance, droplets of iodine solution falling onto instruments could result in iodine allergic reactions in certain patients. For this reason, some surgical kits feature basin portions which are both removable from the surgical kit itself as well as separate from the skin preparation tray, whether or not that skin preparation tray itself is removable from the surgical kit. In such a configuration, it may prove inconvenient to place all the components required to disinfectant the patient's skin in the typical working area provided adjacent the patient.

One problem with removable skin preparation trays is that they can be unstable during use. For instance, the lack of a stable flat surface adjacent the patient will require the practitioner to hold the skin preparation tray in one hand, while manipulating swab implements with the other. Many skin preparation trays are formed from thin thermoplastic material absent adequate reinforcing structure, display less than ideal ergonomic design, and may incorporate pressure pad areas not ideally suited to manipulation without spillage. Depending on the design, they are typically better suited for holding in either the left or right hands of practitioners.

In addition, some skin preparation trays display less than optimal design regarding placement of the various implements, such as swab implements, utilized during a particular procedure. In some trays, the practitioner must unnecessarily rotate or otherwise negotiate the swab implements from their original orientation as provided by the packaging structure on the tray. With both hands typically already occupied, this puts an unnecessary burden on the practitioner. This, of course, could also lead to unwelcome splashing of solution.

All in all, pressure exerted by the practitioner in squeezing excess solution from the swab implement may cause the skin preparation tray to flex, resulting in a high probability of spillage. Depending on where the pressure pad is located in the tray, and depending on the ergonomic fit of the preparation tray against the support provided by a practitioner's hand, the practitioner may be unable to manipulate the swab implement or the tray itself without spilling solution. While conventional skin preparation trays may be suited to either left-handed or right-handed practitioners, there would be a significant cost savings in manufacture if universal manipulability as well as stability could be incorporated in one design.

III. SUMMARY OF THE INVENTION

An improved skin preparation tray for a skin disinfection procedure is provided. The skin preparation tray, which may be retained on a support surface or held in either the left hand or the right hand of the user, can be incorporated as a removable component of a surgical kit.

The skin preparation tray includes a relatively planar sheet surface having pairs of opposed sides, and configured to be held in the hand of a user. The sheet surface may include at least one finger or digit opening formed on an opposed side of the sheet surface to facilitate a user's grasp when the tray is held in the open hand. The skin preparation tray is provided with a plurality of embossments for receiving various components of a skin disinfection procedure. For example, a basin embossment defining a recess may be provided for receiving a quantity of antimicrobial solution. One or more swab embossments define recesses for receiving one or more swab implements used for applying the antimicrobial solution to the skin of a patient. The swab embossments may be configured to receive the swab implements in an optimum position for facilitating a practitioner's manipulation during the various steps of the disinfection procedure.

The skin preparation tray further includes a pressing surface to assist the practitioner in controlling the quantity of antimicrobial solution absorbed by the swab implements. The pressing surface, which may be formed as an embossment defining a recess in the planar sheet of the tray, may incorporate one or more fluid conducting channels. The pressing surface, disposed for fluid communication with the basin embossment, is located on the planar sheet substantially in an area amenable to support by either the left or right hands of a practitioner. Thus, the pressing surface is supported by the open hand of the practitioner, allowing the practitioner to utilize the pressing surface to compress the swab implements without undue flex in the tray.

In use, the skin preparation tray may be supported by a surface or in either the left hand or the right hand of a practitioner. The one or more digit openings allow the user's fingers to grasp opposed sides of the sheet while supporting the sheet in the open palm. The pressing surface itself is supported in the open hand, so that a practitioner can apply a desired amount of force in compressing the swab implement against the pressing surface without risk of flex in the preparation tray. Hence, spillage of the solution is largely avoided.

If desired, one or more strengthening ribs may be incorporated into the planar sheet to enhance structural integrity. In one aspect, the strengthening ribs can be formed as rib embossments in the planar sheet communicating with one or more of the swab embossments and the pressing surface of the tray. A vertically oriented finger tab may also be provided as a convenient way to lift the preparation tray from the surgical kit, and to otherwise handle the preparation tray during use.

IV. BRIEF DESCRIPTION OF THE DRAWINGS

The invention sill now described in greater detail by way of reference to the appended drawings, wherein.

V. DETAILED DESCRIPTION OF THE PREFERRED EMBODIMENTS

Figure 9:
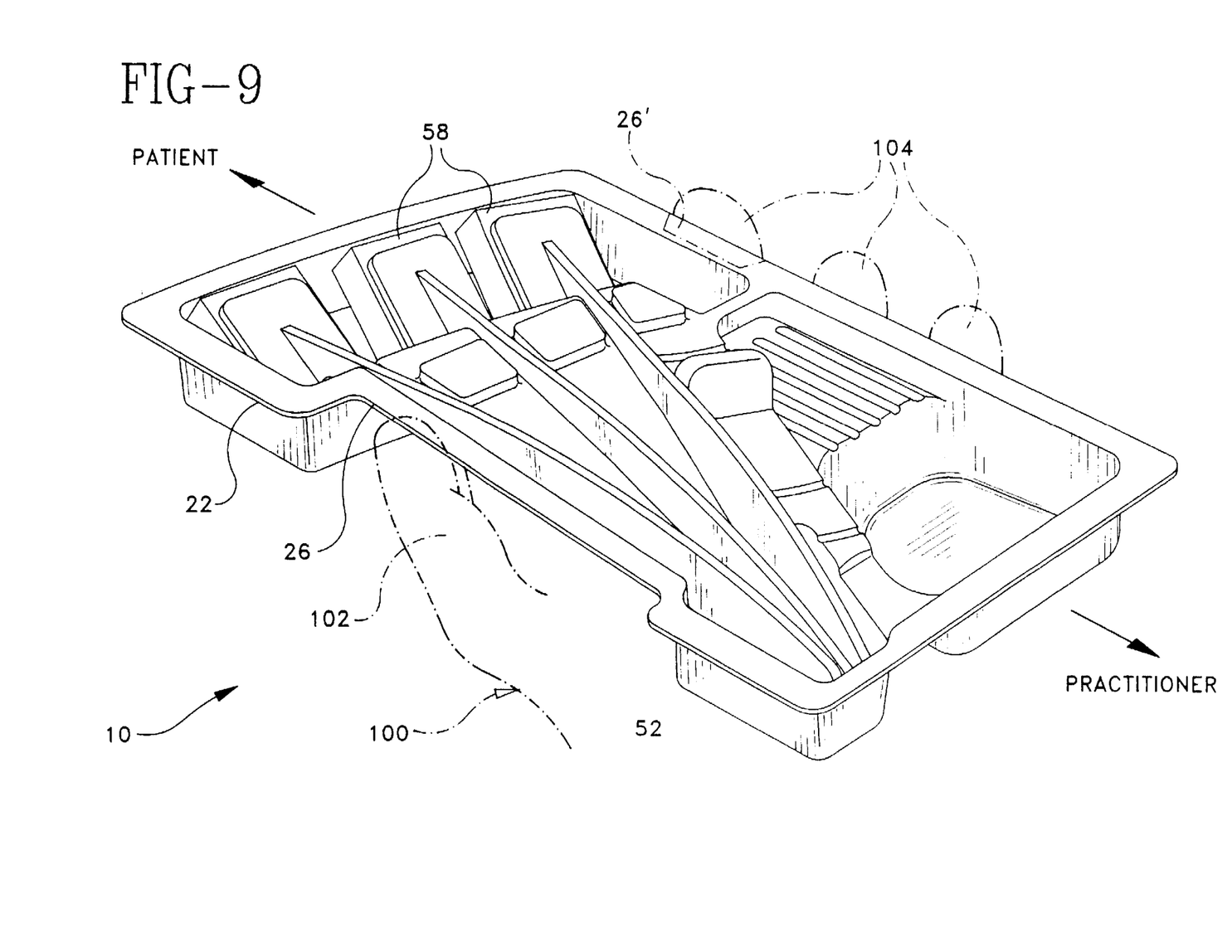
FIGS. 9 and 10 are perspective views depicting, respectively, the skin preparation tray supported by either the left (FIG. 9) or right (FIG. 10) hands of a user.
Figure 10:
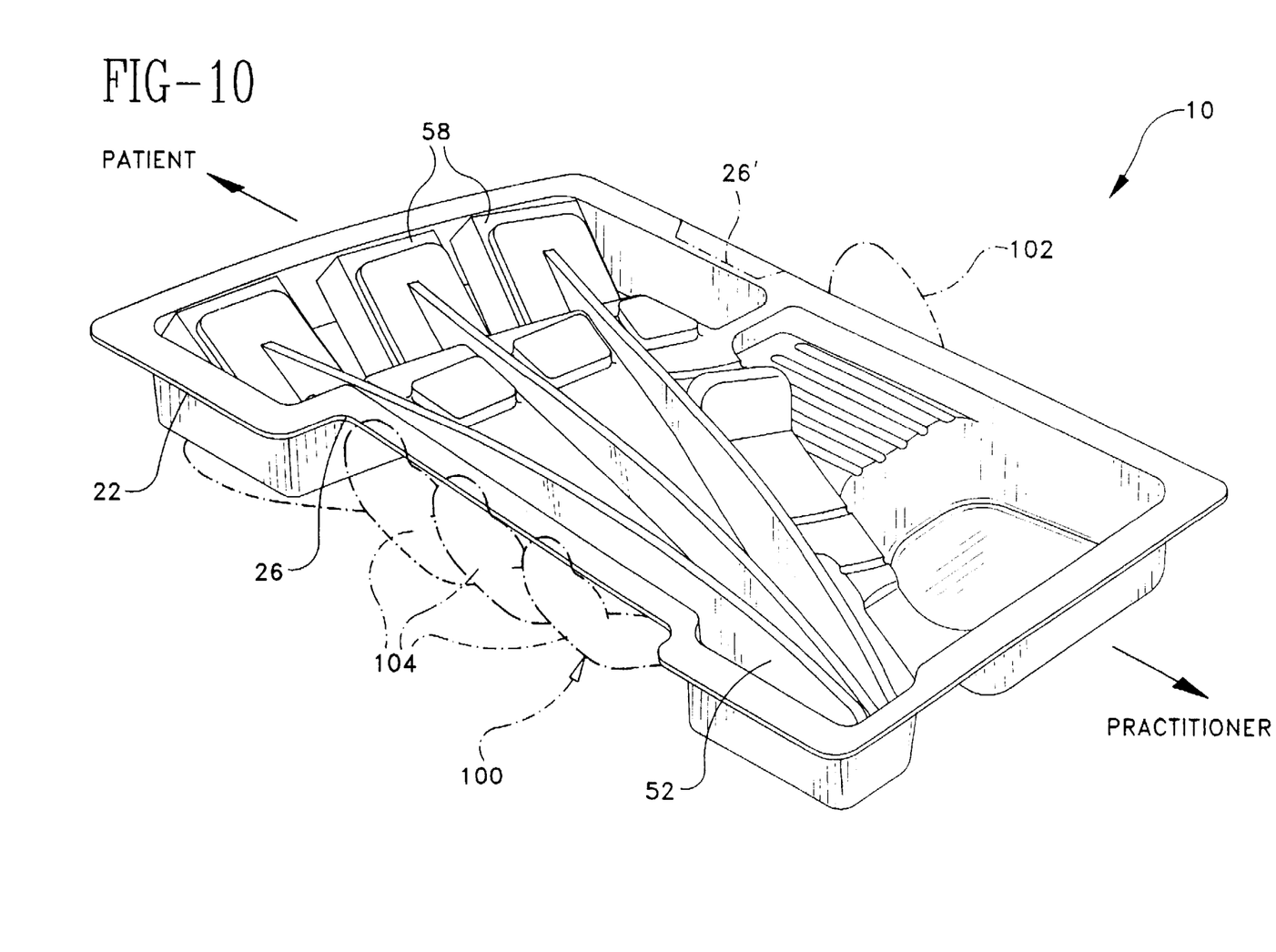

Turning now to the drawings, where like numerals denote like components, FIGS. 1-10 depict one embodiment of a skin preparation tray 10 in accordance with the present invention. The skin preparation tray, which may be unitarily molded from a thermoplastic material, includes a relatively planar surface or sheet 20. Sheet 20 includes pairs of opposed sides 22, 24, preferably configured to allow a practitioner to hold tray 10 in the hand. If desired, sheet 20 may be provided with at least one finger or digit opening 26 cut or otherwise formed in an opposed side of the planar sheet 20. Here, digit opening 26 is shown formed in an opposed side 22. As depicted in FIGS. 9 and 10, skin preparation tray 10 may be supported by either the left (FIG. 9) or right (FIG. 10) open hands 100 of a user. Digit opening 26 provides an opening along an opposed side 22 for accommodating the thumb digit 102 or a pinky, ring, index or forefinger digit 104 of the open hand. If desired, to further enhance the manipulability of skin preparation tray 10—for instance, where a user may display an open hand 100 of smaller than average size—an additional digit opening 26' may be provided on the opposed side 22 opposite digit opening 26. A substantially vertically oriented finger tab 60 may also be provided on sheet 20 to enable a practitioner to readily grip and manipulate skin preparation tray 10.

Figure 1:
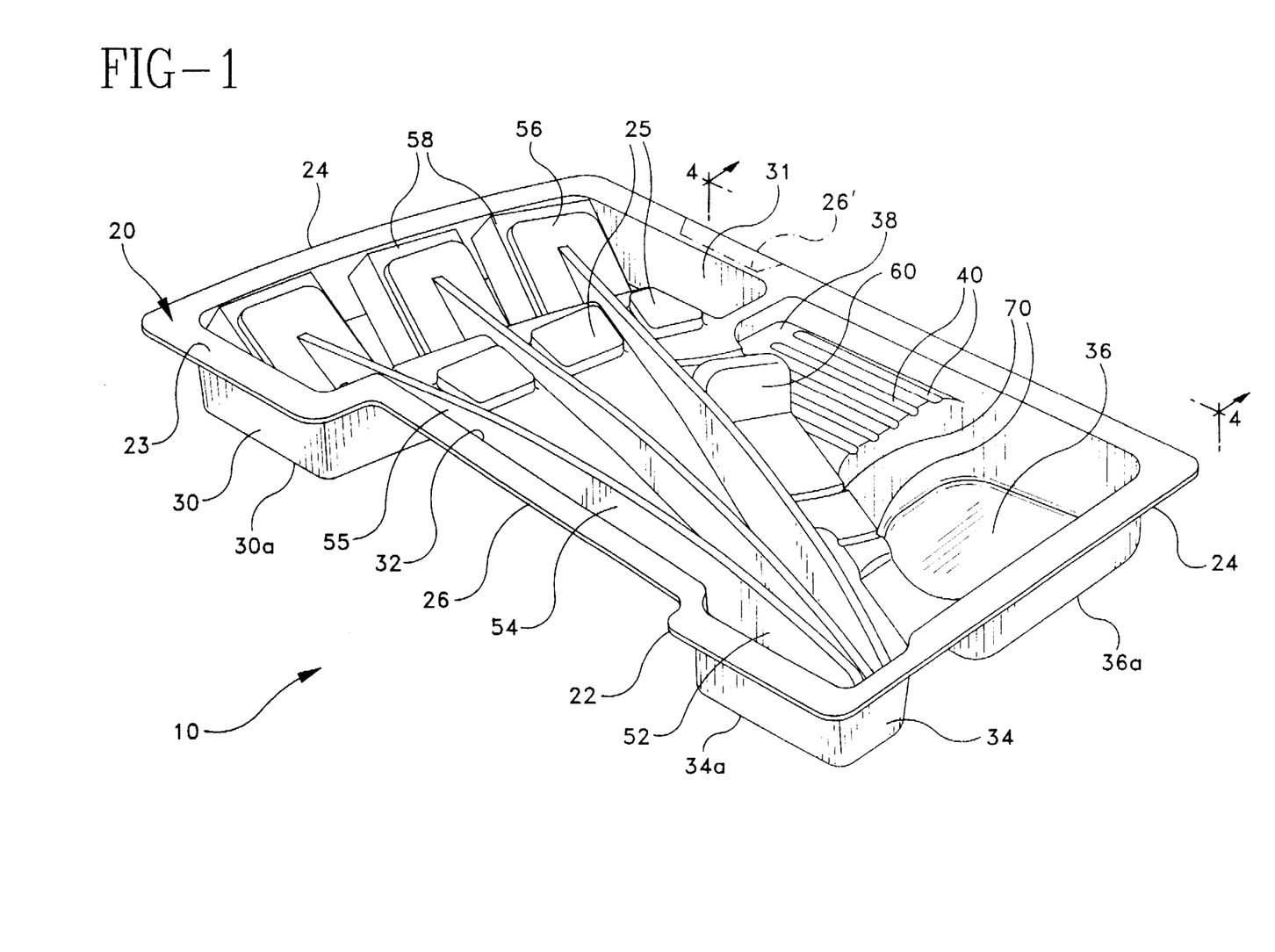
FIG. 1 is a perspective view of one embodiment of a skin preparation tray in accordance with the invention together with a number of swab implements held in swab embossments on the tray.
Figure 2:
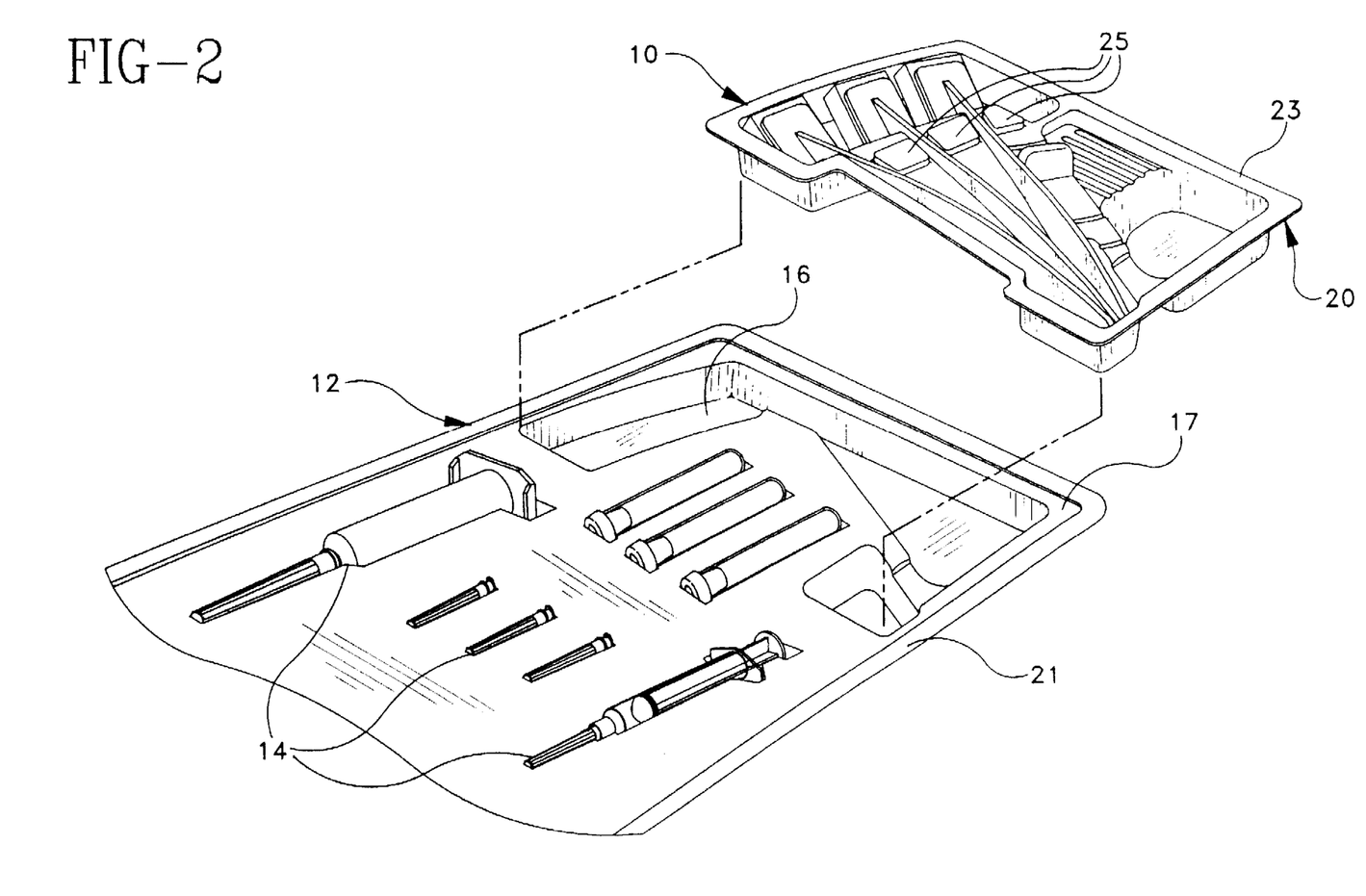
FIG. 2 is a perspective view of the skin preparation tray of FIG. 1 depicting its removability from a surgical kit.
Figure 3:
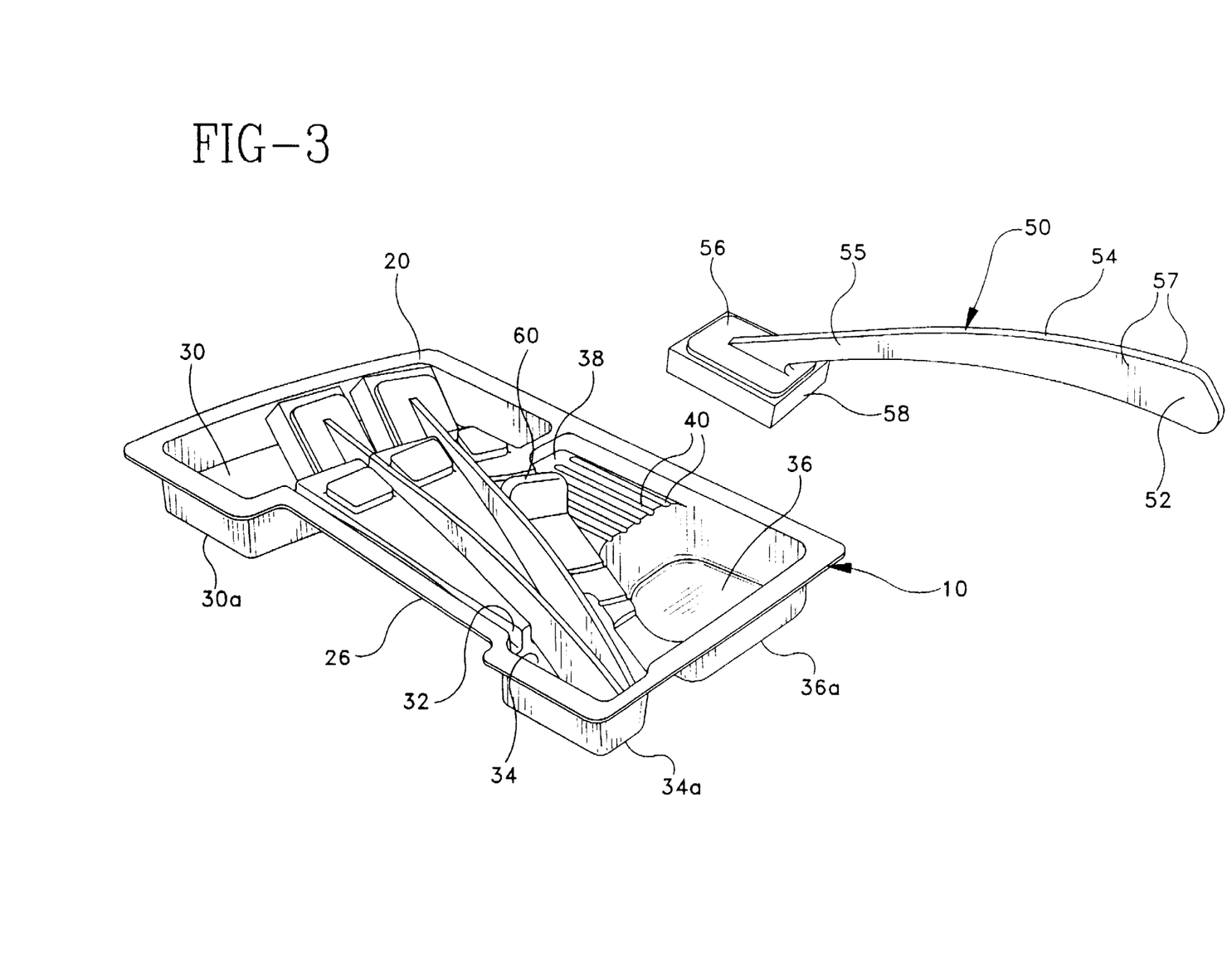
FIG. 3 is a perspective view of the skin preparation tray of FIG. 1 illustrating a swab implement removed from swab embossments on the tray.
Figures 4, 5:
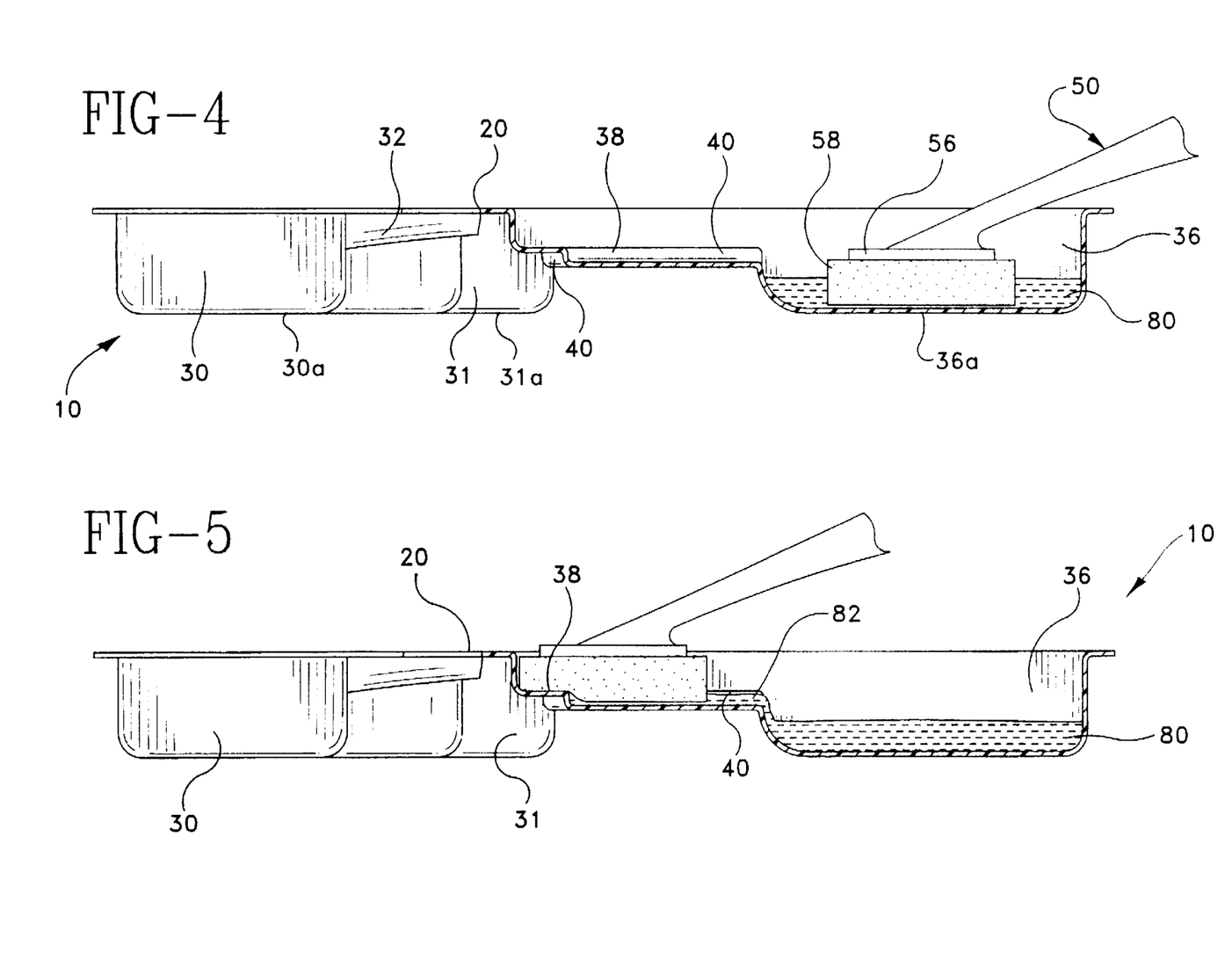
FIG. 4 partial cross-sectional view taken along line 4—4 of FIG. 1, illustrating dipping a swab implement into the basin embossment of the tray so as to absorb a quantity of solution held in the basin embossment.
FIG. 5 is a second partial cross-sectional view of the skin preparation tray of FIG. 4, illustrating compressing the swab implement against the pressing surface of the tray, with excess solution flowing from the swab implement back to the basin embossment.
Figure 6:
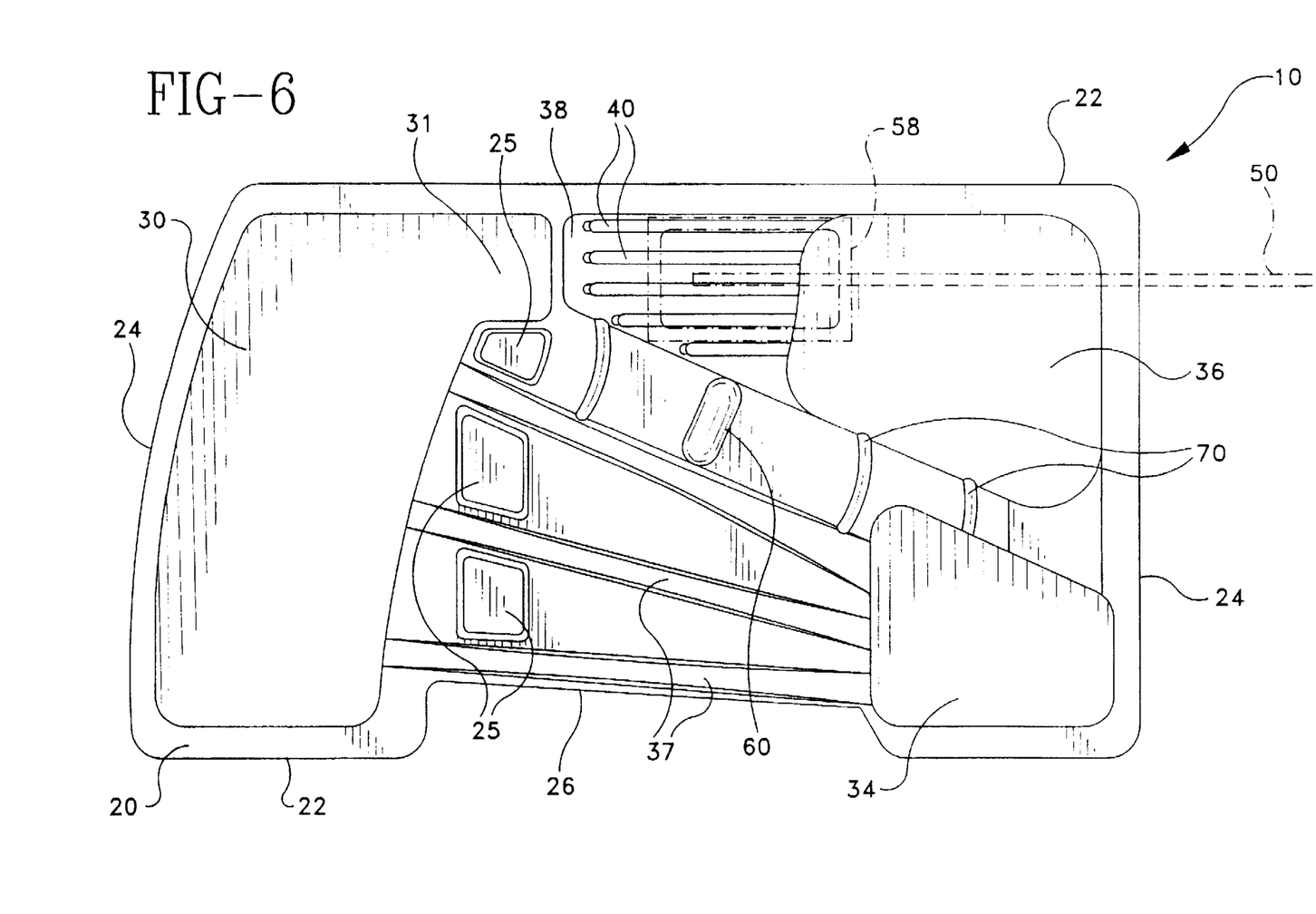
FIG. 6 is a top view of the skin preparation tray of FIG. 1, absent swab implements in the swab embossments but illustrating, in phantom, a swab implement compressed against the pressing surface.
Figure 7:
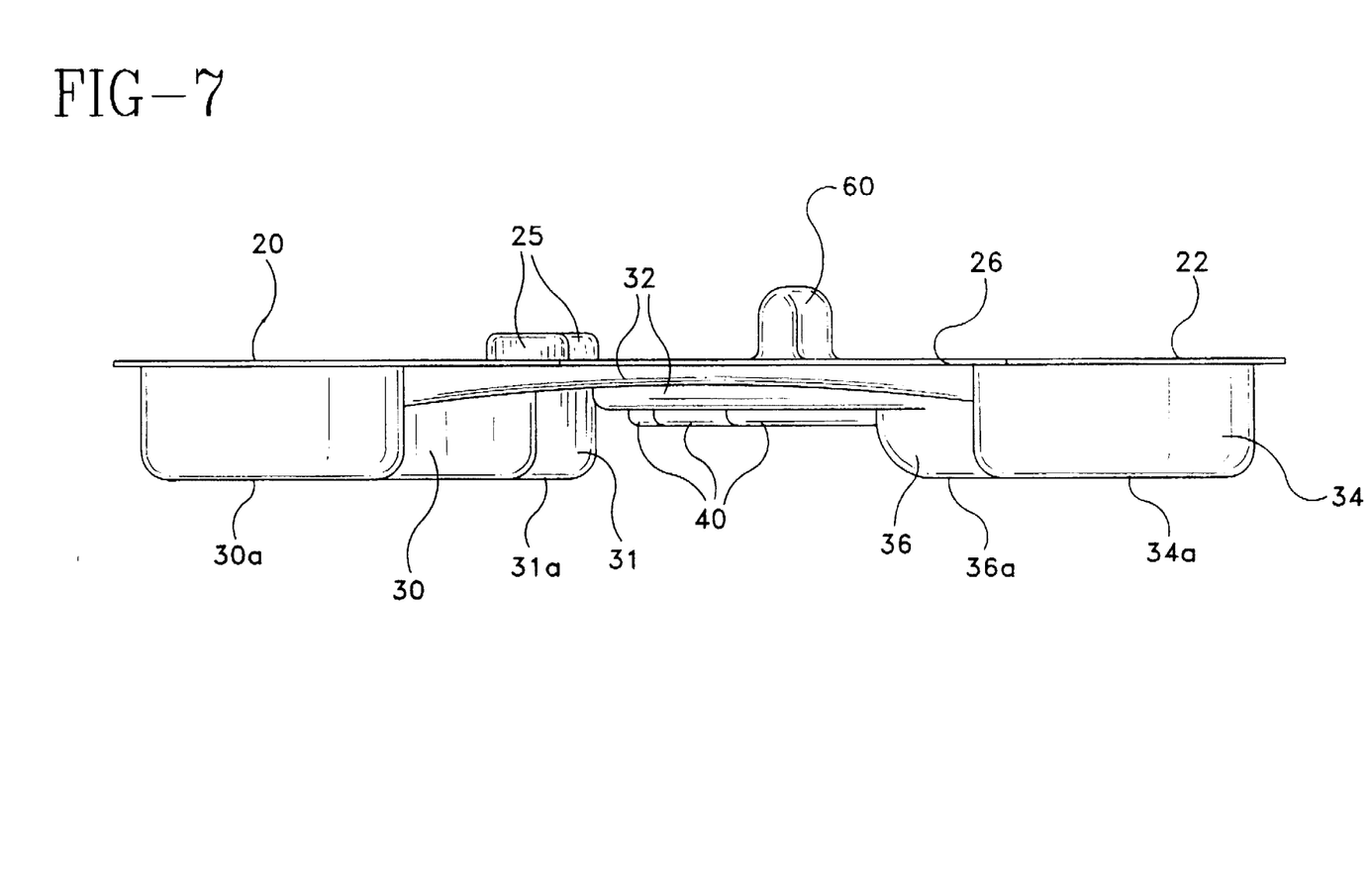
FIG. 7 is a side view of the of the skin preparation tray absent swab implements.
Figure 8:
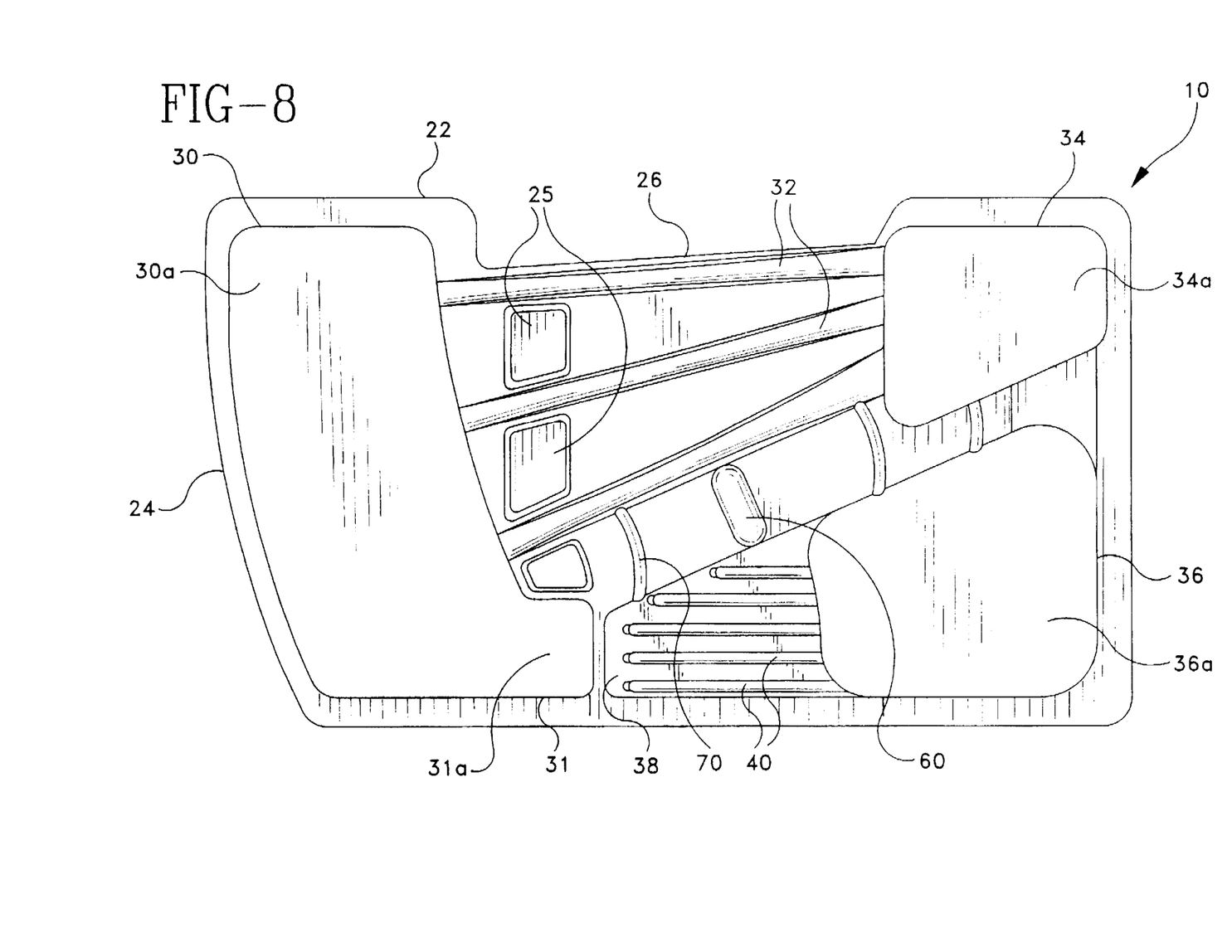
FIG. 8 is a bottom view of the skin preparation tray.

Skin preparation tray 10 may be configured as a removable component of a surgical kit 12. As shown in FIG. 2, surgical kit 12 may feature various implements 14, such as syringes, blood collection tubes, and the like, utilized for a given surgical procedure. The skin preparation tray may be retained in surgical kit 12 in a recessed portion 16 shaped to accommodate the particular shape and structure imparted to various portions of skin preparation tray 10. In one configuration, rim portion 23 of planar sheet 20 may be supported by a ledge portion 17 in surgical kit 12. As thus configured, the skin preparation tray may be contained within surgical kit 12 in a co-planar manner with a perimeter portion 21 of the surgical kit. If desired, spacers 25 may be incorporated on the surface of sheet 20 to help isolate skin preparation tray 10 and the various implements held thereby from gauzes, wraps, pads or other items (not shown) which may be placed over the tray in completing surgical kit 12. The overall design of surgical kit 12 and skin preparation tray 10 promotes compactness, together with ease of packaging and handling.

Skin preparation tray 10 may be provided or otherwise formed with a plurality of embossments defining recesses for retaining various of the implements or components utilized during the skin procedure. One use of skin preparation tray 10 is for a disinfection procedure involving an antimicrobial solution, such as iodine solution, which is applied by a practitioner with surgical swab implements. Examples of such swab implements are represented by the numeral 50 in the figures. While swab implements 50 may assume a variety of shapes or structures known to the skilled artisan, in one configuration swab implements 50 include a relatively elongate, preferably flat handle 54 having a free end 52 and an opposed end 56. Elongate handle 54 features a pair of relatively wide, flat sides 57 adapted to be grasped by the digits 102, 104 of a user. A curved section 55 is provided along the elongate handle 54 which terminates at opposed end 56. A solution-absorptive foam pad 58, typically bonded or otherwise attached to opposed end 56 of swab implement 50, is provided to absorb and apply a quantity of antimicrobial solution to a patient. Here, curved section 55, together with opposed end 56, orient the foam pad at an angle respective of elongate handle 54 (see FIG. 3).

For a given swab implement 50, it would be advantageous to place the swab implement on skin preparation tray 10 in a location best facilitating or otherwise optimizing a practitioner's manipulation and use of the swab implement. Accordingly, for the configuration of swab implement 50 herein illustrated, skin preparation tray 10 is provided with a number of swab embossments 30, 32 and 34 that define various recesses for receiving the various portions defining the structure of swab implement 50. A first embossment 34 defining a recess is provided adjacent one opposed side 24 of planar sheet 20. First embossment 34 includes a bottom surface 34a disposed beneath sheet 20. As herein shown, first embossment 34 receives free ends 52 of swab implements 50. One or more elongate embossments 32 emanate from first embossment 34, with each individual elongate embossment 32 defining a recess for receiving in an upright manner an individual elongate handle 54 of a swab implement 50. Elongate embossments 32 terminate in a second embossment 30 adjacent an opposed end 24 of sheet 20. As herein shown, second embossment 30 receives opposed ends 56 and foam preparation pads 58 of the swab implements. Like first embossment 34, second embossment 30 also features a bottom surface 30a likewise disposed beneath sheet 20.

The depths of the recesses defined by the respective swab embossments 30, 32 and 34 may be chosen such that free ends 52 of the swab implements are substantially retained in the recess defined by first embossment 34, foam pads 58 are substantially received within the recess defined by second embossment 30, and elongate handles 54 are held in an upright manner preferably substantially co-planar with sheet 20 of the tray and positioning sides 57 for ready digital access by a practitioner. While providing good digital access for the swab implements, this overall configuration also contributes to the conservation of packaging space in surgical kit 12.

To further facilitate a practitioner's digital manipulation of individual swab implements 50, it will be seen that second embossment 30 may be formed in an arcuate manner across the opposed end 24 of sheet 20. As illustrated, by radiating each of elongate embossments 32 in a fan-like manner from first embossment 34, elongate handles 54 of the swab implements may be spaced apart from one another to provide a practitioner impediment-free digital access to each of the individual swab implements 50. Additionally, this configuration further contributes to conserving packaging space in surgical kit 12; for instance, spacing each of swab implements 50 parallel to one another would typically require more space.

All in all, then, elongate handle 54 of the swab implement is held in an upright manner from the surface defined by sheet 20, so that the sides 57 of the elongate handle can be easily grasped by the digits of a practitioner. When the tray 10 is held in the open hand 100 of a practitioner, it will be seen that foam pads 58 are pointed away from the practitioner and in the direction of the patient. This positioning eliminates the need for a practitioner to unnecessarily rotate or otherwise manipulate swab implements 50 from an original packing position in skin preparation tray 10 during the various stages—i.e., solution absorption, compression, and patient application—of the procedure.

It will be realized, of course, by the skilled artisan that other configurations of swab embossments other than swab embossments 30, 32, 34 are possible. For instance, one or more of the individual swab embossments 30, 32 and 34 may be combined with one another. Also, in lieu of a multiple embossment configuration, one general swab embossment may be formed or otherwise configured to retain in whole swab implements 50.

Skin preparation tray 10 is further provided with a basin embossment 36 that defines a depth for retaining a quantity of an antimicrobial solution 80, such as an iodine solution, that may be provided from an external source. Basin embossment 36 features a bottom surface 36a disposed beneath sheet 20. As shown in FIGS. 1, 3, 7 and 8, each of the bottom surfaces 30a, 34a, and 36a of swab embossments 30, 34 and basin embossment 36 are preferably substantially co-planar so as to facilitate the stability of preparation tray 10 when placed on a surface.

A practitioner desiring to apply a solution such as antimicrobial solution 80 to a patient during a medical procedure will lift one of swab implements 50 from the tray, dipping the foam pad 58 into basin embossment 36 so as to absorb a quantity of solution 80 into the pad. It is typical that pad 58 may absorb a greater quantity of solution 80 than necessary or desirable for application to the patient. Accordingly, skin preparation tray 10 is further provided with a pressing surface 38 against which foam pad 58 of the swab implement can be compressed by a practitioner to control the amount of solution absorbed or otherwise retained by the pad.

As depicted, pressing surface 38 is located on sheet 20 intermediate the pair of opposed ends 22 of the sheet. Pressing surface 38, herein depicted as an embossment in the surface of sheet 20, is located for fluid communication with basin embossment 36. One or more fluid conducting channel embossments 40 may be provided on pressing surface 38 so as to help direct fluid flow into basin embossment 36. The depth of the recess defined by pressing surface 38 is preferably less than the depth of the recess defined by basin embossment 36. Thus, excess solution 82 compressed from foam pad 58 of the swab implement will flow back into the quantity of solution 80 held by basin embossment 36 (see FIGS. 4 and 5).

While pressing surface 38 is here shown as an embossment, it will be realized by the skilled practitioner that, if desired, pressing surface 38 may be provided in a co-planar manner with sheet 20. Channel embossments 40 may be retained to direct excess solution 82 into the basin embossment 36. Ridges or other barriers (not shown) may be placed around the perimeter of pressing surface 38 to prevent the inadvertent splashing of solution from the pressing surface during compression of foam pad 58.

It will be realized that by placing pressing surface 38 intermediate the opposed sides 22 of preparation tray 10, the pressing surface 38 may be readily supported by the open hand 100 of either the right (FIG. 10) or left (FIG. 9) hands of a practitioner. Accordingly, there is a reduced chance of flex in tray 10, with a concomitant reduction in spillage of the solution either retained in basin embossment 36 or splashed from pressing surface 38. Thus, pressing surface 38 provides the practitioner with a ready way to regulate the quantity of solution 30 held by the swab implements without undue risk of spillage of the solution.

To further reduce flex and otherwise enhance the stability of skin preparation tray 10, particularly where the tray is placed on a surface, one or more strengthening ribs 70 may be provided on sheet 20. Here, strengthening ribs 70 are formed as rib embossments communicating with one of the swab embossments 32, 34 and with basin embossment 36. If desired, strengthening ribs 70 could also be formed as solid ribs with the sheet 20.

As also seen, to further reduce the probability of flex when applying force to the pressing surface, second embossment 30 may be extended into a contiguous area 31 adjacent the area where pressing surface 38 is located on sheet 20. Contiguous area 31 of the second embossment may be provided with a bottom surface 31a, likewise disposed beneath sheet 20. Bottom surface 31a can be made co-planar with bottom surfaces 30a, 34a, and 36a to further enhance the stability of the skin preparation tray when placed on a surface.

It will be realized by the skilled artisan that the shapes, structure, and placement of the various swab embossments 30, 32, 34 may be altered or revised, as need or desire dictate, to accommodate an appropriate number of swab implements shaped differently than swab implements 50 illustrated herein; the principle consideration, that of placing the swab implements on tray 10 in a manner facilitating a practitioner's manipulation, will remain unaffected. All of the various embossments illustrated herein can be formed unitarily with planar sheet 20 or, as need or desire dictate, formed as separate components for affixation to a sheet 20 separately manufactured. Also, supporting legs or other appendages may be provided with or otherwise substituted for bottom surfaces 30a, 34a, 36a, or 31a which are co-planar, so as to stably support the skin preparation tray on a surface. It will be further realized that sheet 20 and the various embossments can be shaped for accommodation in a given area of a given surgical kit 12.

The preparation tray 10 in accordance with the invention thus serves to address the concerns hereinbefore mentioned. By providing a pressing surface that is both in fluid communication with a basin as well as supported by the open hand of a practitioner, the tray is less amenable to flex, thereby preventing the splashing of solution and the attendant harms which can arise therefrom. Structural details further contribute to stability when the tray is placed on a surface. All of the components necessary to conduct the procedures are placed together in a compact manner. The swab implements are retained on the preparation tray in a manner most convenient to maneuver-free manipulation by the practitioner, both in grasping the swab implements from the tray for dipping into the basin, and for thereafter removing excess solution and advancing the swab implement towards the desired skin area of the patient. The preparation tray may be retained with equal ease by either hand of a user, all the time retaining stability in the pressing surface.

It will be appreciated and understood by those skilled in the art that further and additional forms of the invention may be devised without departing from the spirit and scope of the appended claims, the invention not being limited to the specific embodiments shown.

We claim:

1. A kit useful for preparing a patient for catheterization comprising:
    an implement tray having a plurality of recesses therein for holding a plurality of implements for preparing a patient for catheterization, wherein one of said recesses is shaped to receive a removable preparation tray;
    a removable preparation tray holdable in a user's hand for use in the preparation of the patient involving a solution and one or more swab implements absorptive of a quantity of said solution,
    at least one swab to receive, to deliver and to apply the solution to the patient's skin;
    said removable preparation tray comprising a relatively planar sheet having a top surface, a bottom surface and opposed sides, said removable tray being sized and ambidextrously configured to be held between the fingers and thumb of either of a user's hands, and wherein said removable tray includes at least one swab embossment forming a recess for receiving said one or more swab implements and a basin embossment having a depth for receiving a quantity of the solution, and wherein said at least one of said swab embossments and said basin embossment define co-planar bottom surfaces spaced at said opposed sides of said removable tray sufficient to enable said removable preparation tray to be stood stable on a work surface; and
    said basin embossment further including a pressing surface to allow the user to control the quantity of solution absorbed by said one or more swab implements by the user's compression of said one or more swab implements against said pressing surface, said pressing surface being fluidly communicable with said basin embossment to collect a surplus of the solution in said basin embossment; and
    said pressing surface being located intermediate said opposed sides of said removable tray so that when said removable tray is held between the thumb and fingers of the hand the user, said pressing surface is supported by the palm of the user's hand.

2. The kit of claim 1 wherein further comprising a container of a preparation solution.

3. The kit of claim 1 wherein at least one of said opposed sides of said removable tray defines an opening disposed to accommodate the digits of the user's hand when said removable tray is held in the user's hand.

4. The kit of claim 1 wherein said pressing surface of said removable tray defines one or more channels disposed to communicate with said basin embossment to deliver the surplus solution compressed from said one or more swab implements to said basin embossment.

5. The of kit of claim 4 wherein said pressing surface of said removable tray further defines a recess having a depth and wherein said depth defined by said basin embossment is greater than the depth defined by said pressing surface.

6. The kit of claim 1 wherein said removable tray further comprises a finger grip substantially vertically disposed from said top surface.

7. The kit of claim 1 wherein said removable tray further comprises one or more spacers.

8. The kit of claim 1 wherein said removable tray is formed from a thermoplastic material.

9. The kit of claim 1 wherein said one or more of said swab implements each include an elongate handle end and an opposed end provided with a solution absorptive pad.

10. The kit of claim 1 wherein said removable tray further comprises:
    a first embossment adjacent said basin embossment defining a recess for receiving the handle end of each of said one or more swab implements; and
    at least one elongate embossment defining a recess for receiving another of said one or more swab implements.

11. The kit of claim 10 wherein said elongate embossment of said removable tray communicates with said basin embossment.

12. The kit of claim 10, wherein said basin embossment is located adjacent one side of said removable tray and said elongate embossment being located at an opposed side of the removable tray.

13. The kit of claim 10, wherein the recess defined by said first embossment is configured to retain each of the handle ends of swab implements substantially adjacent one another, wherein an another embossment defines a relatively arcuate recess configured to retain each of the absorptive pads of the swab implements in spaced relationship to one another.

14. The kit of claim 1 wherein said removable tray further comprises at least one strengthening rib.

15. The kit of claim 14 wherein at least one of said strengthening ribs of said removable tray fluidly communicates with at least one of said swab embossments.

16. The preparation tray of claim 14, wherein said one or more strengthening ribs comprises a rib embossment communicating with at least one of said one or more swab embossments.

17. A kit useful for preparing a patient for catheterization comprising:

an implement tray having a plurality of recesses therein for holding a plurality of implements for preparing a patient for catheterization, wherein one of said recesses is shaped to receive a removable preparation tray;

a removable preparation tray holdable in a user's hand for use in the preparation of the patient involving a solution and one or more swab implements absorptive of a quantity of said solution, a container of a preparation solution, at least one swab to receive, to deliver and to apply the solution to the patient's skin;

said removable preparation tray comprising a relatively planar sheet having a top surface, a bottom surface and opposed sides, said removable tray being sized and ambidextrously configured to be held between the fingers and thumb of either of a user's hands, wherein at least one of said opposed sides of said removable tray defines an opening disposed to accommodate the digits of the user's hand when said removable tray is held in the user's hand, and wherein said removable tray includes at least one swab embossment forming a recess for receiving said one or more swab implements and a basin embossment having a depth for receiving a quantity of the solution, and wherein said at least one of said swab embossments and said basin embossment define co-planar bottom surfaces spaced at said opposed sides of said removable tray sufficient to enable said removable preparation tray to be stood stable on a work surface; and said basin embossment further including a pressing surface to allow the user to control the quantity of solution absorbed by said one or more swab implements by the user's compression of said one or more swab implements against said pressing surface, said pressing surface being fluidly communicable with said basin embossment to collect a surplus of the solution in said basin embossment, wherein said pressing surface of said removable tray defines one or more channels disposed to communicate with said basin embossment to deliver the surplus solution compressed from said one or more swab implements to said basin embossment, and wherein said pressing surface of said removable tray further defines a recess having a depth and wherein said depth defined by said basin embossment is greater than the depth defined by said pressing surface; and said pressing surface being located intermediate said opposed sides of said removable tray so that when said removable tray is held between the thumb and fingers of the hand the user, said pressing surface is supported by the palm of the user's hand.

* * * * *